US012098991B2

(12) United States Patent
Urey et al.

(10) Patent No.: US 12,098,991 B2
(45) Date of Patent: Sep. 24, 2024

(54) METHOD AND APPARATUS FOR DETECTING NANOPARTICLES AND BIOLOGICAL MOLECULES

(71) Applicants: KOC UNIVERSITESI, Istanbul (TR); BAHCESEHIR UNIVERSITESI, Istanbul (TR)

(72) Inventors: Hakan Urey, Istanbul (TR); Ugur Aygun, Istanbul (TR); Ayca Yalcin Ozkumur, Istanbul (TR)

(73) Assignees: KOC UNIVERSITESI, Istanbul (TR); BAHCESEHIR UNIVERSITESI, Istanbul (TR)

( * ) Notice: Subject to any disclaimer, the term of this patent is extended or adjusted under 35 U.S.C. 154(b) by 661 days.

(21) Appl. No.: 17/276,844

(22) PCT Filed: Sep. 17, 2018

(86) PCT No.: PCT/TR2018/050501
§ 371 (c)(1),
(2) Date: Mar. 17, 2021

(87) PCT Pub. No.: WO2020/060501
PCT Pub. Date: Mar. 26, 2020

(65) Prior Publication Data
US 2021/0348998 A1 Nov. 11, 2021

(51) Int. Cl.
*G01J 9/02* (2006.01)
*G01B 9/02* (2022.01)
(Continued)

(52) U.S. Cl.
CPC ..... *G01N 15/0227* (2013.01); *G01B 9/02041* (2013.01); *G01N 33/56911* (2013.01);
(Continued)

(58) Field of Classification Search
CPC ......... G01N 15/0227; G01N 33/56911; G01N 33/56983; G01N 2015/0038; G01N 21/45;
(Continued)

(56) References Cited

U.S. PATENT DOCUMENTS

| 8,334,976 B2 * | 12/2012 | Carney | G02B 21/0056 356/336 |
|---|---|---|---|
| 2003/0067539 A1 * | 4/2003 | Doerfel | H04N 13/351 348/E13.043 |

(Continued)

FOREIGN PATENT DOCUMENTS

| CA | 2594311 A1 | 1/2008 | |
|---|---|---|---|
| KR | 20040029836 A * | 4/2004 | ........... G06F 3/0317 |

(Continued)

*Primary Examiner* — Mohamed K Amara
(74) *Attorney, Agent, or Firm* — Bayramoglu Law Offices LLC

(57) ABSTRACT

Disclosed are an optical interferometry apparatus for detection of dielectric nanoparticles and a method for enhancing visibility of the nanoparticles. An imaging system for detection of dielectric nanoparticles includes at least one light source for illumination, a detector array or a camera for image capture, an objective lens, a sample substrate and a computing unit. The sample substrate is capable of carrying sub-wavelength particles smaller than the diffraction resolution limit of the imaging system, and the imaging system includes a movable means which moves the sample substrate in the axial direction such that depthwise different images are captured at different axial distances from the sample substrate to the objective lens. The computing unit computes a correlation image using the depth images wherein the sub-wavelength particles become resolvable and appear with higher contrast in the correlation image.

24 Claims, 12 Drawing Sheets

(51) Int. Cl.
*G01N 15/0227* (2024.01)
*G01N 33/569* (2006.01)
*G02B 21/02* (2006.01)
*G02B 21/36* (2006.01)
*G06T 7/571* (2017.01)
*H04N 25/71* (2023.01)
*H04N 25/76* (2023.01)
*G01N 15/00* (2006.01)

(52) U.S. Cl.
CPC ....... *G01N 33/56983* (2013.01); *G02B 21/02* (2013.01); *G02B 21/367* (2013.01); *G06T 7/571* (2017.01); *H04N 25/71* (2023.01); *H04N 25/76* (2023.01); *G01N 2015/0038* (2013.01); *G06T 2207/10056* (2013.01)

(58) Field of Classification Search
CPC .. G01B 9/02041; G02B 21/02; G02B 21/367; G06T 7/571; G06T 2207/10056; H04N 25/71; H04N 25/76
See application file for complete search history.

(56) References Cited

U.S. PATENT DOCUMENTS

| | | | | |
|---|---|---|---|---|
| 2009/0009191 | A1* | 1/2009 | Little, Jr. | G01N 22/00 324/639 |
| 2010/0067005 | A1* | 3/2010 | Davis | G01N 21/21 702/30 |
| 2011/0176731 | A1* | 7/2011 | Fukushi | G06T 7/32 382/170 |
| 2014/0307261 | A1* | 10/2014 | Popescu | G01N 21/4795 356/450 |
| 2015/0153558 | A1* | 6/2015 | Ozcan | G01B 9/04 348/79 |
| 2017/0270688 | A1* | 9/2017 | Nobayashi | G01C 3/08 |
| 2018/0045937 | A1* | 2/2018 | Xu | G06T 7/571 |
| 2022/0277441 | A1* | 9/2022 | Schlaudraff | G02B 21/12 |
| 2022/0284574 | A1* | 9/2022 | Wagner | C12M 41/46 |
| 2023/0160806 | A1* | 5/2023 | Zhao | G01N 15/1434 250/459.1 |

FOREIGN PATENT DOCUMENTS

| | | |
|---|---|---|
| TW | 201144753 A | 12/2011 |
| WO | 2012004388 A1 | 1/2012 |
| WO | 2015021332 A1 | 2/2015 |
| WO | 2017041809 A1 | 3/2017 |

* cited by examiner

METHOD AND APPARATUS FOR DETECTING NANOPARTICLES AND BIOLOGICAL MOLECULES

CROSS REFERENCE TO THE RELATED APPLICATIONS

This application is the national phase entry of International Application No. PCT/TR2018/050501, filed on Sep. 17, 2018, the entire contents of which are incorporated herein by reference.

TECHNICAL FIELD

The present invention relates to an optical interferometry apparatus for detection of dielectric or metallic nanoparticles. In particular, the present invention concerns a method and a device for enhancing visibility of the nanoparticles.

BACKGROUND

Direct detection and quantification of synthetic and naturally occurring nanoparticles is critical in many applications such as drug delivery, disease diagnostics and therapy, treatment monitoring and development of new biomarkers. Rapid and sensitive detection of viruses is crucial for preventing a potential outbreak. Another important class of biological nanoparticles is exosomes which are released from cells to carry proteins and nucleic acids. Exosomes have dimensions between 30-100 nm and have attracted considerable interest recently due to their potential applications in early diagnosis, such as cancer and neurodegenerative diseases.

Clinically relevant nanoparticles have relatively low concentration; hence instead of ensemble detection, single particle level detection is required. Optical detection of these nanoparticles is a challenging problem due to their small size and low dielectric index. Therefore, direct observation based on elastic scattering-based techniques is difficult. In order to visualize these nanoparticles, a contrast mechanism is required. In optical techniques popular contrast mechanism is to use fluorescence detection. However, utilization of this label based technique has its shortcomings. Photobleaching limits the observation time and because not all of the biological nanoparticles are fluorescent, a labeling step is required which can affect the final results.

To overcome limitations of labeling, elastic scattering-based detection modalities are preferred where wavelength is conserved upon scattering. Among these methods, dark field techniques which are based on elimination of all background light, is not applicable to subwavelength sized objects. Due to size scaling factor ($1/V^2$, where V is volume of the particle) in Rayleigh scattering, nanoparticle signal would be below the noise limit of detectors. One way to modify this size scaling factor is to use interferometry, where scattering signal is combined with a reference signal.

Interferometry is a circle of relatives of strategies wherein waves, normally electromagnetic waves, are superimposed inflicting the phenomenon of interference with the intention to extract information. Interferometry is a crucial investigative method inside the fields of astronomy, fiber optics, engineering metrology, optical metrology, oceanography, seismology, spectroscopy (and its programs to chemistry), quantum mechanics, nuclear and particle physics, plasma physics, far off sensing, biomolecular interactions, floor profiling, microfluidics, mechanical stress/strain dimension, velocimetry, and optometry.

Interferometers are extensively used in technology and industry for the dimension of small displacements, refractive index changes and surface irregularities. In an interferometer, light from a single source is split into beams that travel special optical paths and then combined once more to generate interference. The resulting interference fringes provide information about the difference in optical path length. In analytical technology, interferometers are used to measure lengths and the form of optical components with nanometer precision; they may be the highest precision length measuring instruments existing. In Fourier transform spectroscopy, interferometers are used to investigate light containing functions of absorption or emission related to a substance or mixture. An astronomical interferometer consists of two or more separate telescopes that combine their signals, offering a resolution equal to that of a telescope of diameter equal to the largest separation between its individual elements.

In the present invention, visibility of nanoparticles in interferometric microscopy is enhanced using defocusing response. With the proposed method which is called Depth Scanning Correlation (DSC) Interferometric Microscopy, the detection of sub 35 nm dielectric particles without using any labels is experimentally demonstrated. This enhanced detection technique can be used to detect biological particles over a range between 15 nm-100 nm where conventional methods are insufficient.

The attempts made in the state of the art to alleviate the problems associated with detection of dielectric nanoparticles are described in the following patents.

International Appl. No. WO2015EP01804 discloses a method of detecting particles after separation of particles based on their specific features, e.g., charge, size, shape, density, as series of single light scattering events created by the individual particles. The particles are separated from each other along the separation path and particles have specific arrival times at the target side depending on the particle features. The detecting step comprises an interferometric sensing of the light scattered at individual particles bound or transient in the detection volume. Parameters of the scattering light signals such as the interferometric contrast are analyzed for obtaining specific particle features, e.g., size, mass, shape, charge, or affinity of the particles. Furthermore, a detection apparatus being configured for detecting particles is described in the mentioned application.

Canadian Appl. No. CA20072594311 discloses an interferometric system and method for quadrature detection of optical characteristics of a sample. The system includes a Mach-Zehnder interferometer providing a variable optical delay between light collected from the sample and reference light. The Mach-Zehnder interferometer has an output M×N coupler with N.gtoreq.3 output ports. Two differential detectors, each having two input ports coupled to a different two of the N output ports of the M×N coupler, produce first and second electrical signals having an interferometric phase shift. A processor is provided for computing real and imaginary parts of a complex refractive index of the sample from the first and second electrical signals by using complex deconvolution.

International Appl. No. WO2011EP61633 discloses a device for three-dimensional imaging by full-field interferential microscopy of a volumic and scattering sample comprising an emission source for emitting an incident wave with low temporal coherence, an imaging interferometer of variable magnification, allowing for the acquisition of at least one first and one second interferometric images resulting from the interference of a reference wave obtained by reflection of the incident wave on a reference mirror and an object wave obtained by backscattering of the incident wave by a slice of the sample at a given depth of the sample, the at least two interferometric images having a phase difference obtained by varying the relative path difference between the object and reference arms of the interferometer, a processing unit for processing said interferometric images making it possible to obtain a tomographic image of said slice of the sample, means for axially displacing the interferometer relative to the sample allowing for the acquisition of tomographic images for slices at different depths of the sample and means for varying the magnification of the imaging interferometer allowing for the acquisition of interferometric images of a slice of the sample for different magnification values.

The present invention aims to increase visibility (contrast) and SNR of the particles, hence sensitivity can be improved. Due to their small scattering cross-section, detection of dielectric nanoparticles using optical techniques is challenging. Scattered field is very weak and generally lower than the noise of the measurement system. To increase the visibility of the particles, interferometric detection techniques are implemented. However, even with these systems, particles with diameters smaller than 50 nm cannot be detected. The sensitivity limit can be improved by using fast cameras, at the expense of cost. Using this approach, in which frame difference method is utilized, only moving nanoparticles can be detected. In another approach, the use of Fourier plane filters is proposed, which complicates the optical system. Furthermore, fabrication of these filters is not straightforward.

The present invention focuses on eliminating the effect of the axial position of particles on the detected signal. The interference signal is scaled with the cube of the radius of the particle; therefore, it can be used for determining the particle size. However, the axial location of the particle also affects the interference signal, which is generally ignored and can lead to wrong quantification results. The particles may be elevated from the surface especially if two- or three-dimensional surface chemistries are employed in tethering the particles on the surface, and this elevation may depend on the environmental conditions including air vs liquid environment, or the temperature, pH, and ionic concentrations employed.

The present invention aims to use a set of defocused images, hence eliminating the need for fine focusing. In traditional interferometric microscopy, high NA objectives are used to image nanoparticles. These objectives have low depth of field, which requires careful focusing and alignment, hence an operator is needed. Any x-y translation can also change the axial position of the sample and re-calibration is also needed. Furthermore, any vibration due to table or building could possibly lead to defocusing and an active feedback mechanism is required.

The present invention targets to eliminate the inhomogeneity in illumination pattern as well as structures in the image due to dust or dirt in optical path. Hence it does not require a reference measurement. Any dirt on optical path can be seen on captured image and can make the quantification difficult in conventional methods. Similarly, optical components can be moved which leads to inhomogeneity in illumination.

SUMMARY

The object of the present invention is to provide an optical interferometry apparatus for detection of dielectric or metallic nanoparticles with enhanced visibility of the nanoparticles, increased SNR, eliminated inhomogeneity in illumination pattern and eliminated need for fine focusing.

The invention relates to a special DSC interferometric microscopy technique for detection of dielectric or metallic nanoparticles. It is described that integration of mechanical actuation to interferometric imaging can be used to further enhance the visibility of the nanoparticles. Utilization of defocusing will give another set of information about the presence of particles due to their unique defocusing response. This response, using correlation analysis, can be used to selectively amplify the particle images, while suppressing the background. It is described that the present system can be used for direct detection of dielectric nanoparticles as small as 33 nm. Furthermore, direct detection of single exosomes is demonstrated. The proposed approach can be used for a wide range of applications where characterization of single individual nanoparticles is required.

In summary, an apparatus that improves visibility of nanoparticles based on a correlation image which is calculated using a series of defocused images is proposed.

BRIEF DESCRIPTION OF THE DRAWINGS

Accompanying drawings are given solely for the purpose of exemplifying an apparatus for high-contrast imaging of sub-wavelength size particles, whose advantages over prior art were outlined above and will be explained in brief hereinafter.

The drawings are not meant to delimit the scope of protection as identified in the claims nor should they be referred to alone in an effort to interpret the scope identified in said claims without recourse to the technical disclosure in the description of the present invention.

FIG. 2A shows orientation of the nanoparticles in the simulations. FIG. 2B shows the nanoparticle contrast calculated. FIG. 2C shows the calculated images of the particle.

FIGS. 5A and 5B show nanoparticles with a diameter of 50 nm that are immobilized on the substrate and imaged without depth scanning correlation (DSC) technique. FIGS. 5C and 5D show nanoparticles with a diameter of 50 nm that are immobilized on the substrate and imaged with depth scanning correlation (DSC) technique.

FIG. 6A shows the correlation image, and FIGS. 6B-6D show the SEM images of the particles identified in the correlation image.

FIG. 7A shows a conventional image and FIG. 7B shows depth scanning correlation image in accordance with this invention.

FIGS. 8B, 8D, 8F, and 8H respectively show the correlation image generated by the analysis using the axial ranges shown in FIGS. 8A, 8C, 8E, and 8G.

REFERENCED PARTS LIST

Figure 1:
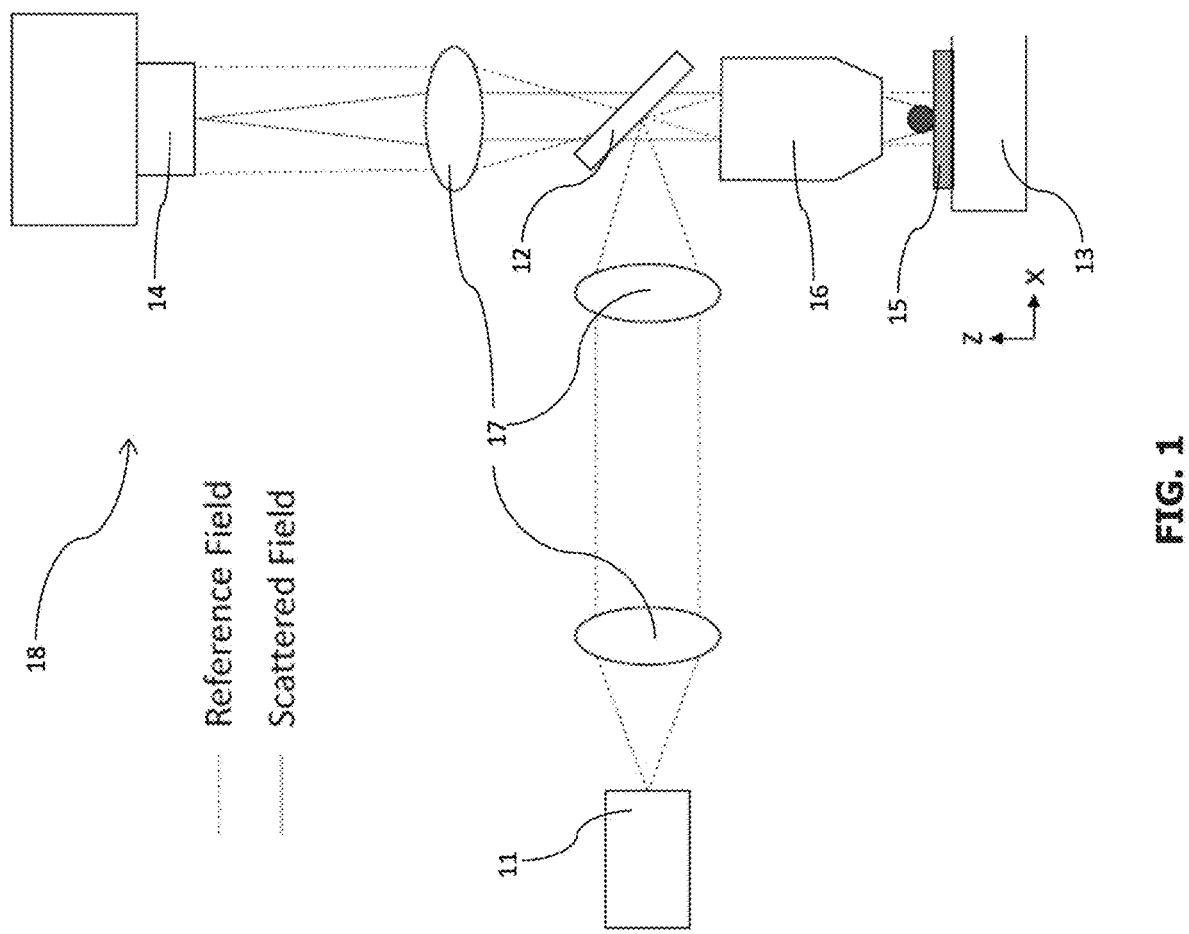
FIG. 1 is an interferometric imaging system for implementing the method in accordance with this invention.

11 Light source
12 Beam splitter
13 Movable means
14 Camera
15 Sample substrate
16 Objective lens
17 Lens
18 Imaging system Abbreviations used in the detailed description of the invention are listed below:

| | |
|---|---|
| $E_{inc}$) | Incident field |
| r) | Reflection coefficient of the sample plate |
| s) | Scattering amplitude of the particle |
| ∅) | Phase difference between reference and scattering fields |
| $I_t(x, y)$) | Pixel's intensity captured at time t |
| R(t)) | Actuation signal's level at time t |
| $\sigma_I$) | Standard deviation of pixel intensity |
| $\sigma_R$) | Standard deviation of actuation signal |

DETAILED DESCRIPTION OF THE EMBODIMENTS

FIG. 1 demonstrates an imaging system (18) for enhancing visibility of nanoparticles according to the present invention. The imaging system (18) comprises various lenses (17) and a processing unit. In a variation, the imaging system (18) can employ a Michelson-type interferometer configuration. It is illuminated by a light source (11), which in a preferred embodiment has, high spatial coherence (small emission area) and high temporal coherence (limited spectral width). Light emitting diodes (LED), VCSELs, and laser light sources can be used for the purpose. The imaging system (18) comprises a detector array, for instance a CCD or CMOS based camera (14), a beam splitter (12) that makes it possible to send into the interferometer the wave emitted by the light source (11) and an objective lens (16). A movable means (13) allows for an axial displacement of a sample substrate (15). The acquisition in depth in the sample is produced by an axial displacement of the sample relative to the camera (14). In a variation, the objective lens (16) is a zoom objective. Wide-field illumination can be provided through sample illuminated in Kohler configuration. In a variation, as a sample substrate (15), Si/SiO$_2$ surface with 100 nm oxide thickness is used. The oxide thickness can be varied and optimized for the wavelengths used in the system to control the interference between the scattered light and the reference light. Scattered field from nanoparticles together with the reference field, reflected from layered substrate is imaged onto the camera (14) using the objective lens (16). Preferably, objective lens (16) is a 40× or higher magnification objective. Detected signal intensity can be written as:

$$I_{det} = |E_{ref} + E_{sca}|^2 = r^2 E_{inc} + s^2 E_{inc} + 2 \cdot r \cdot s \cdot \cos \phi E_{inc} \quad \text{Eq 1}$$

Figure 2B:
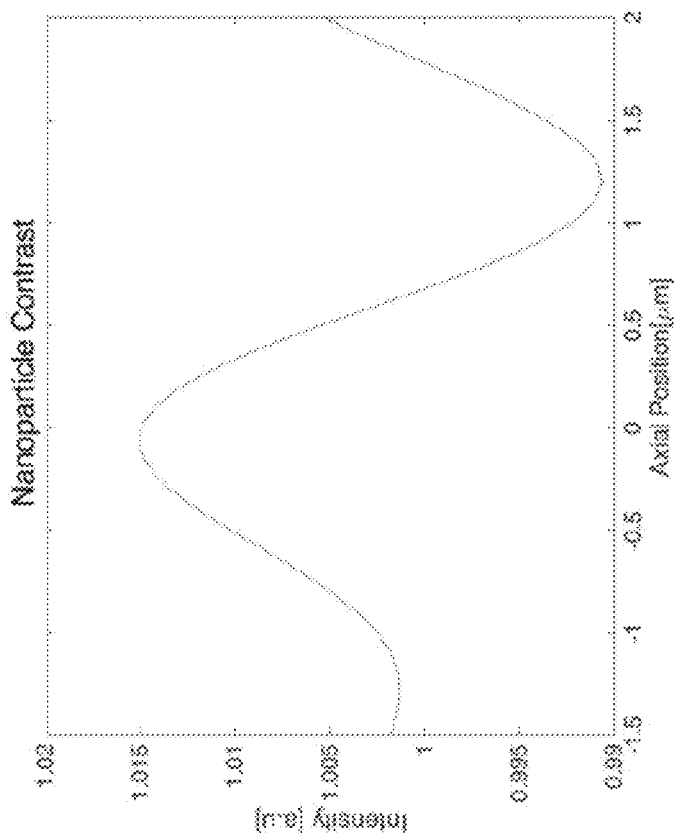
FIGS. 2A-2C show focused and defocused responses of dielectric nanoparticles in accordance with this invention.
Figure 2A:
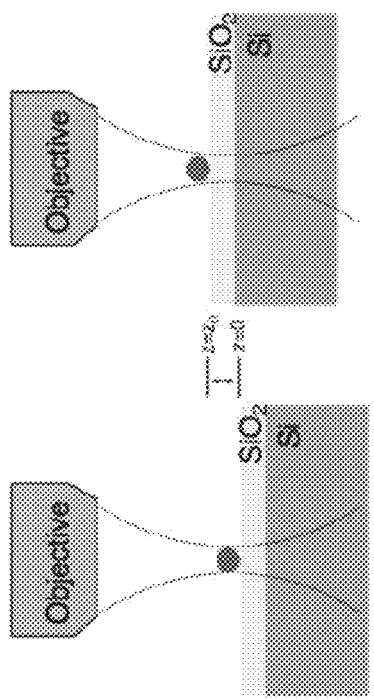
Figure 2C:
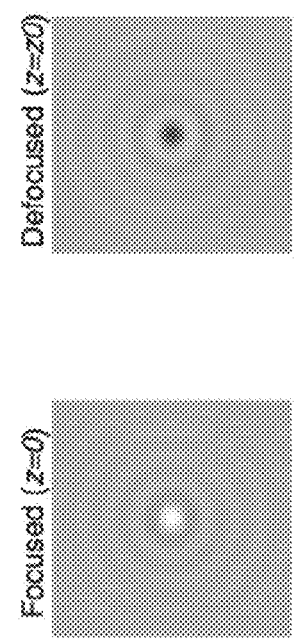

In contrast to purely scattering based techniques where particle signal is scaled with the square of the volume, in interferometric techniques interference term in Eq. (1) is scaled with s and thereby the volume of the particle. Interferometric detection is implemented by using a reflective sample substrate (15). In addition to interferometric enhancement, nanoparticles have unique defocusing response that can be used for further enhancement FIGS. 2A-2C show simulation results of the defocusing response of dielectric nanoparticles on top of sample substrate (15). In the simulations, nanoparticles are modeled as point dipoles with an orientation determined by the illumination field (FIG. 2A). Due to spatial incoherence of the light source (11), for instance LED, illumination field is modeled as incoherent sum of plane waves covering the illumination angle defined by NA (numerical aperture) of the objective lens (16). For each of the plane wave image of the dipole is calculated using the PSF (point spread function) of the imaging system (FIG. 2B). In the final step, image of the particle is calculated by summing the individual dipole images (FIG. 2C).

Figure 3:
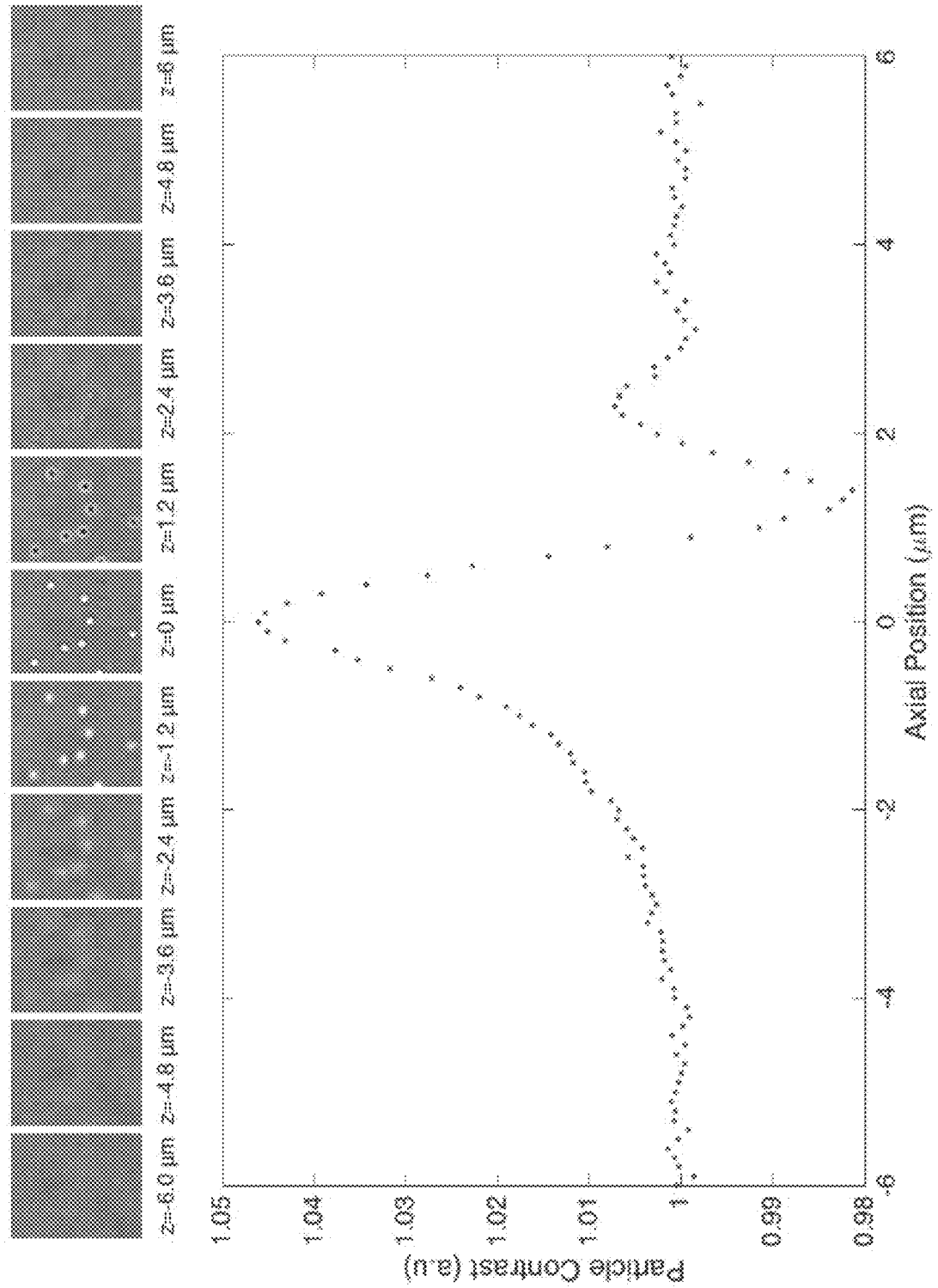
FIG. 3 shows calculated contrast values for different axial positions of the sample stage in accordance with this invention.

FIG. 3 represents focusing response of polystyrene nanoparticles with 100 nm diameter. In this variation, to capture defocused particle images, sample is placed on a movable means (13) and axial position is modulated with intervals of 100 nm. Image of nanoparticle is highly sensitive to axial position of the sample. Particles can induce positive or negative contrast according to its axial position.

Figure 4:
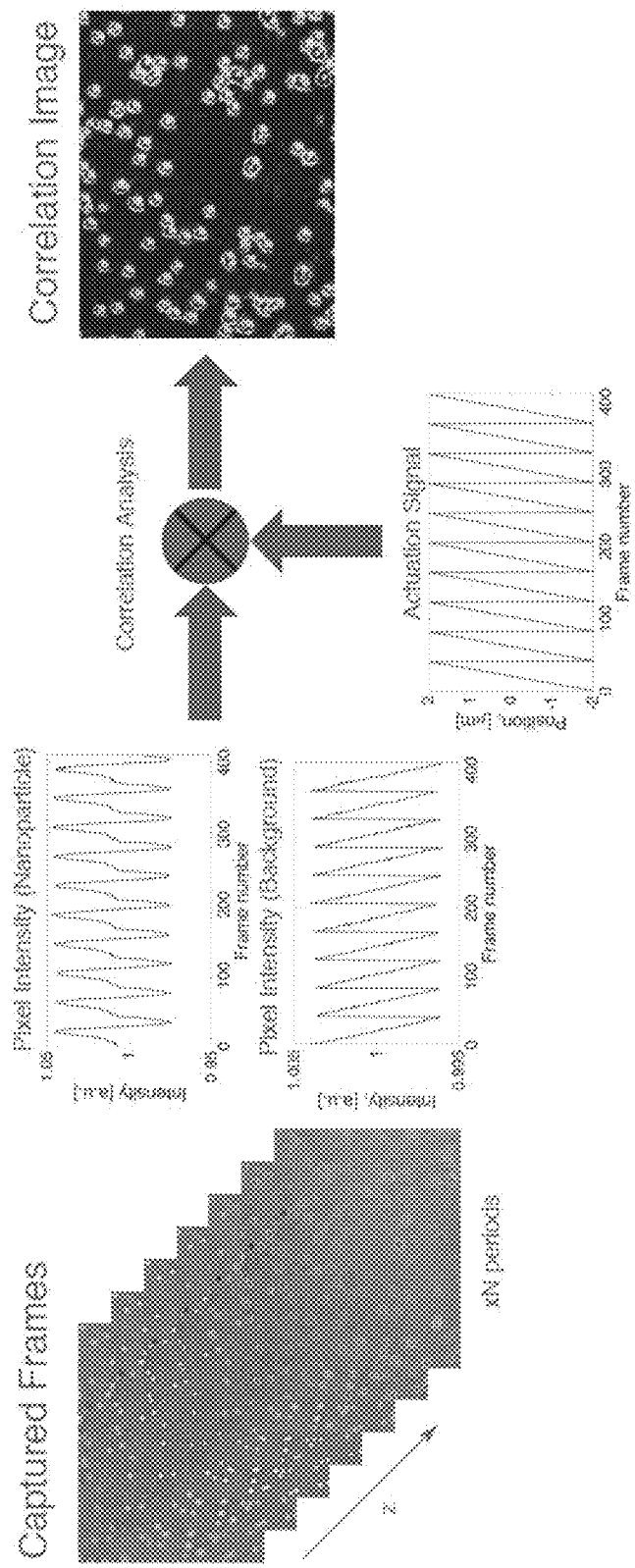
FIG. 4 shows depth scanning correlation enhancement procedure in accordance with this invention.
Figures 5A, 5B, 5C, 5D:
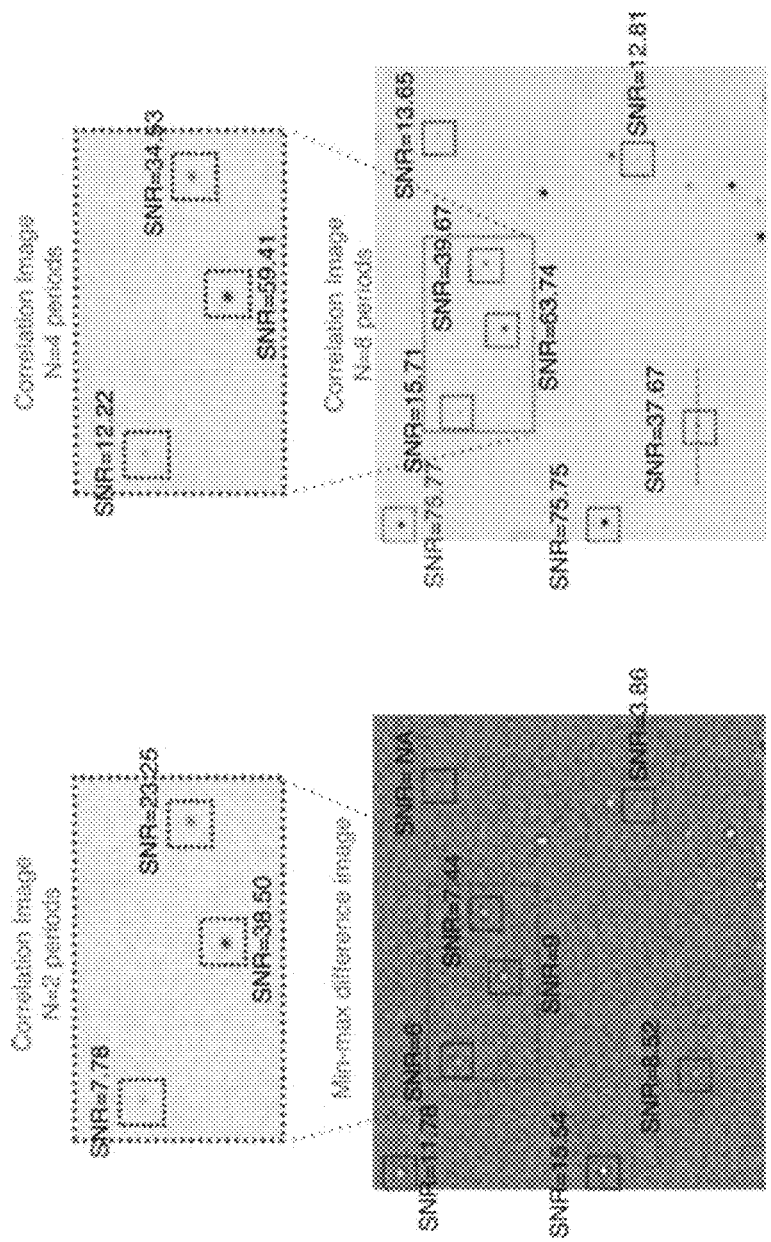
FIGS. 5A-5D show visibility enhancement for nanoparticles in accordance with this invention.
Figure 6A:
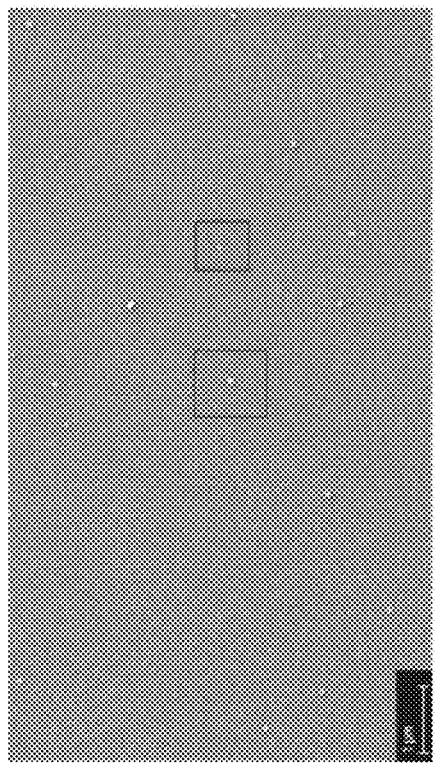
FIGS. 6A-6D show a comparison between correlation image and SEM image in accordance with this invention.
Figure 6B:
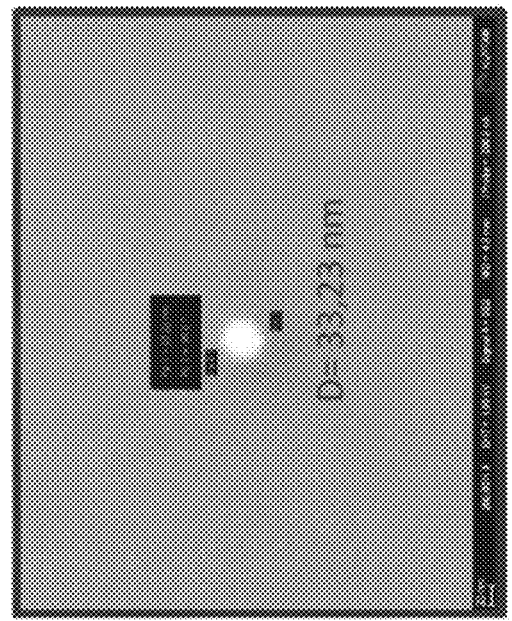
Figure 6C:
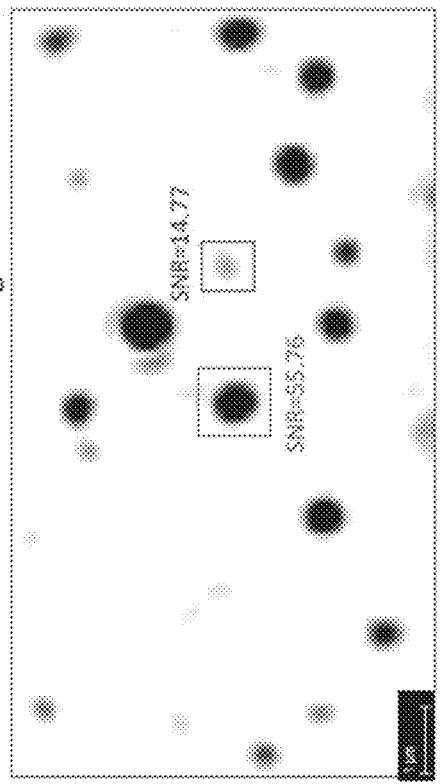
Figure 6D:
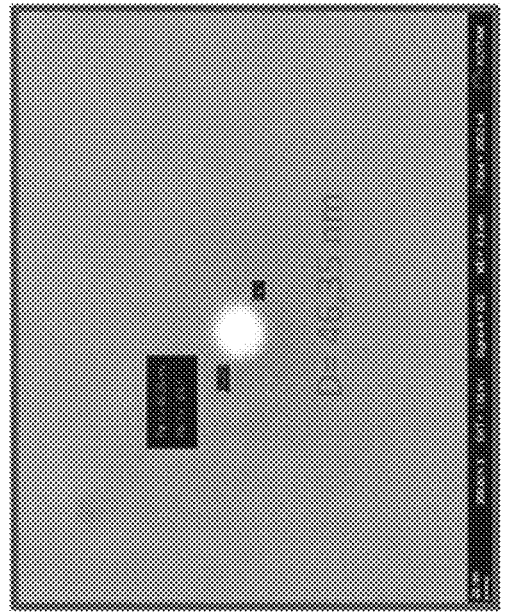

FIG. 4 shows discrimination particles from the background, movable means (13) is actuated towards the camera (14) with a sawtooth pattern and a cross-correlation analysis is performed between actuation signal and every pixel in the captured images. Pearson correlation coefficient ρ is calculated for every pixel location (x, y) as follows:

$$I_{corr}(x, y) = |\rho(x, y)|^2 = \left| \frac{1}{N-1} \sum_{t=t_0}^{t_{N-1}} \left( \frac{I_t(x, y) - \overline{I(x, y)}}{\sigma_I} \right) \left( \frac{R(t) - \overline{R}}{\sigma_R} \right) \right|^2 \quad \text{Eq 2}$$

where $I_t(x,j)$ is the pixel's intensity captured at time t, R(t) actuation signal's level at t, $\sigma_I$ and $\sigma_R$ are the standard deviation of pixel intensity and actuation signal respectively; <I(x,y)> and <R> mean values of pixel intensity and actuation signal over one period. Correlation image is composed of square of the correlation values of each pixel. According to Eq. (2), ρ can get values between −1 and 1. Zero means highly uncorrelated signal, one means highly correlated signal. In order to obtain a highly correlated signal for the background signal to distinguish nanoparticles from the background noise level, illumination is slightly tuned to have a converging beam on the sample to vary the background with the movement of the movable means (13). Hence, inverse relation between background signal intensity and axial position of the sample is achieved (<%0.5 variation in background signal over one period). Final correlation image can represent highly correlated (background) pixels as white and uncorrelated (nanoparticle) pixels as black.

FIGS. 5A-5D show enhanced visibility of the nanoparticles with higher SNR. Particles with a diameter of 50 nm are immobilized on the substrate and imaged with and without depth scanning correlation (DSC) technique. After an initial rough focusing, the movable means (13) is actuated with 100 nm steps for a total of 2 µm in sawtooth pattern. DSC technique enhances the signal to noise ratio (SNR) of individual nanoparticles. SNR can be further increased, by increasing the number of periods in the analysis.

FIGS. 6A-6D demonstrate that depth-scanning correlation enhancement can also be used to detect even smaller nanoparticles. Developed optical system is capable of detecting samples (for example; polystyrene nanoparticles) as small as 33 nm in diameter with SNR of about 14, which is also verified by SEM imaging. Assuming the volume dependence of the signal, the detection of nanoparticles smaller than 20 nm nanoparticles seem possible.

Figures 7A, 7B:
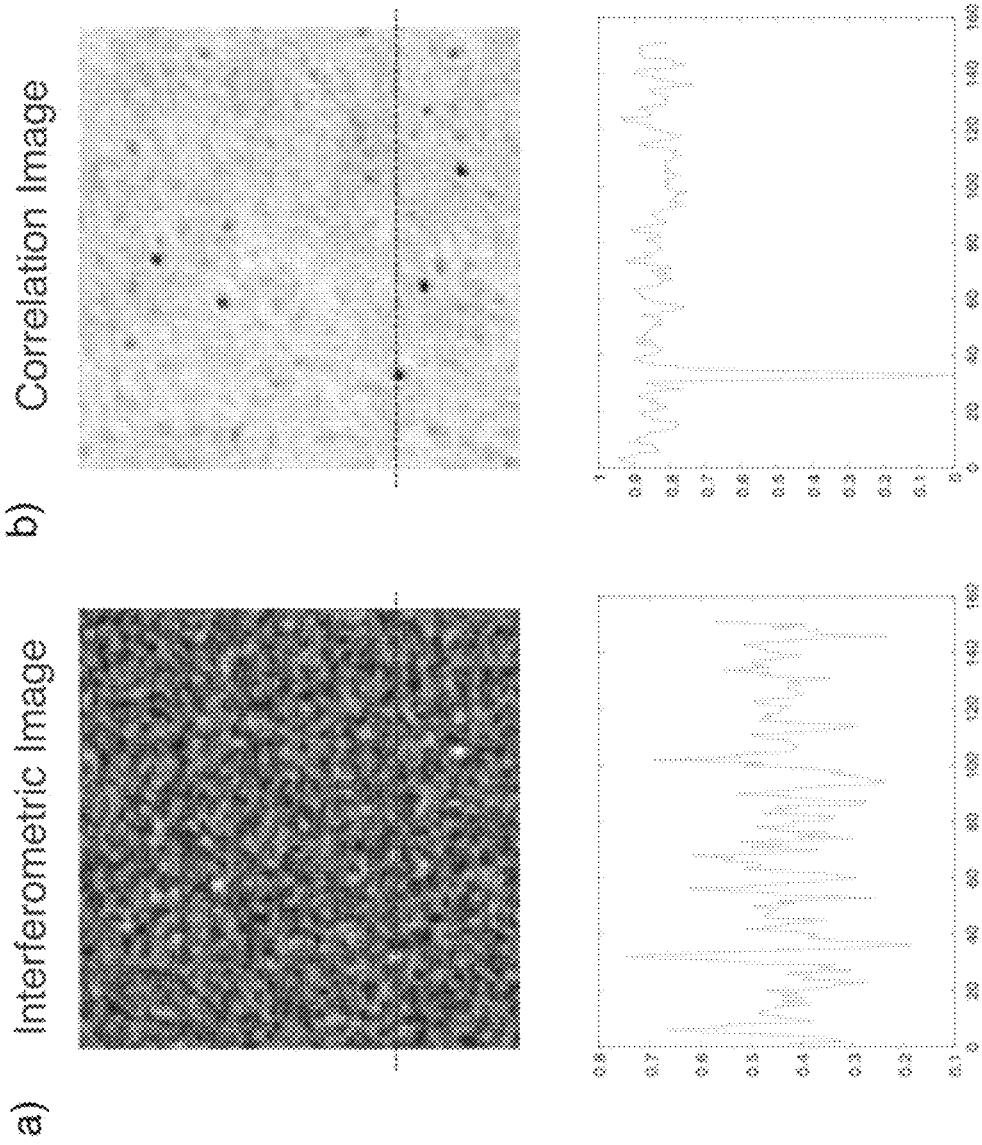
FIGS. 7A-7B show a comparison between correlation image and interferometric image.
Figure 8A:
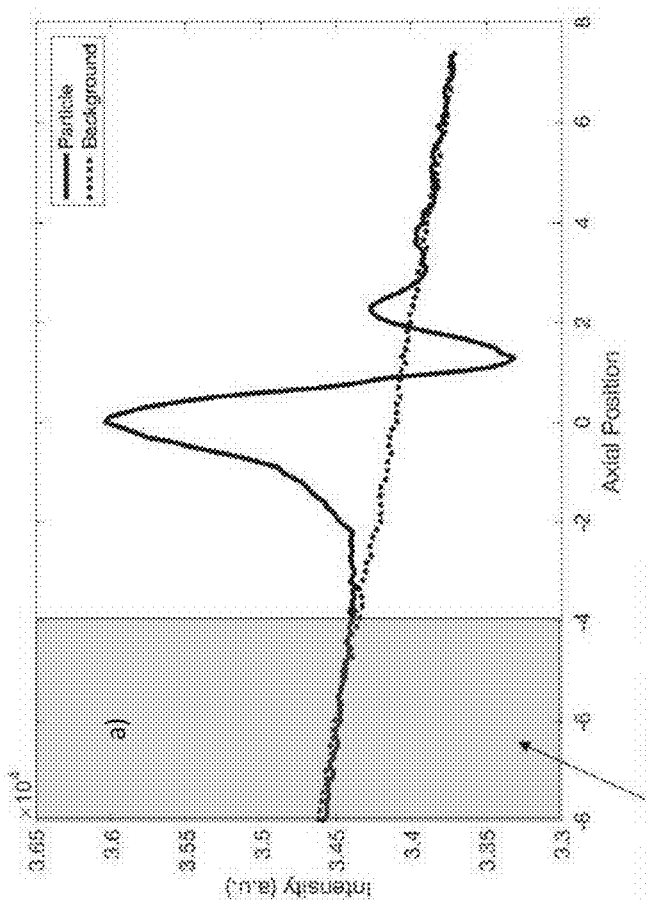
FIGS. 8A-8H show intensity variation with respect to defocus for particle (black line) and background (dotted line) pixels in accordance with this invention.
Figure 8B:
Figure 8D:
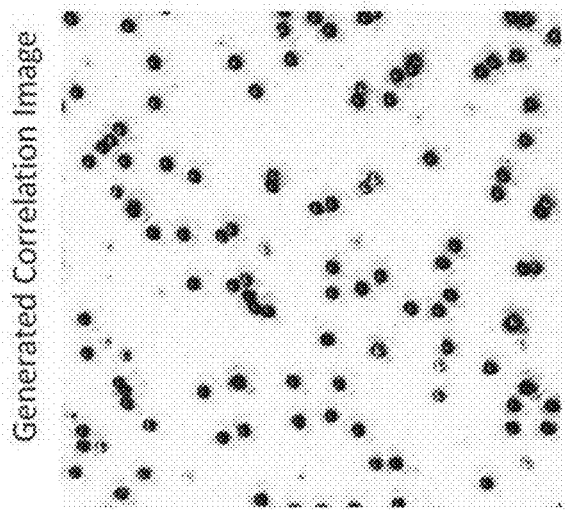
Figure 8C:
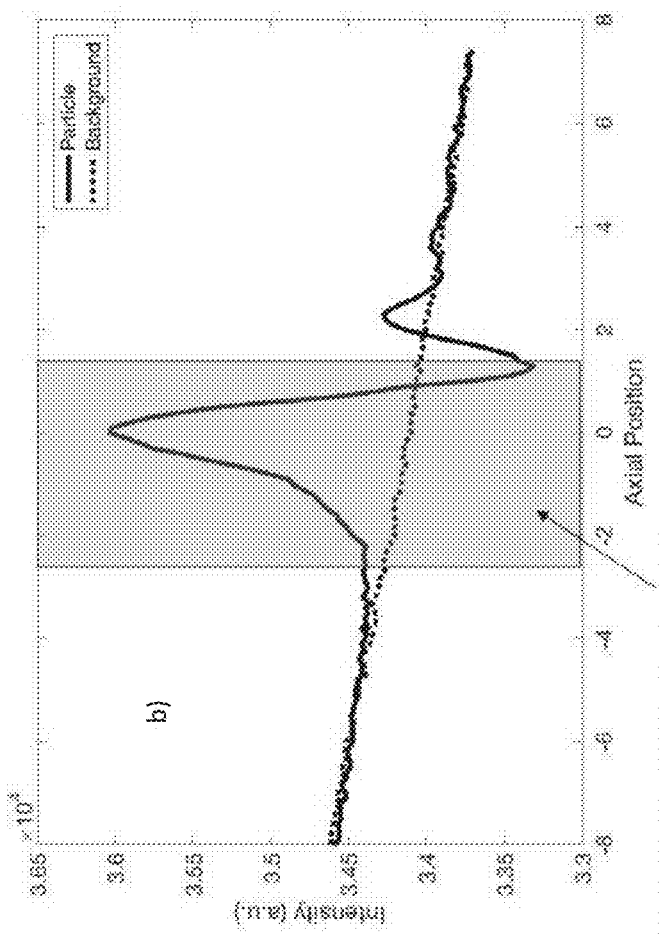
Figures 8E, 8F:
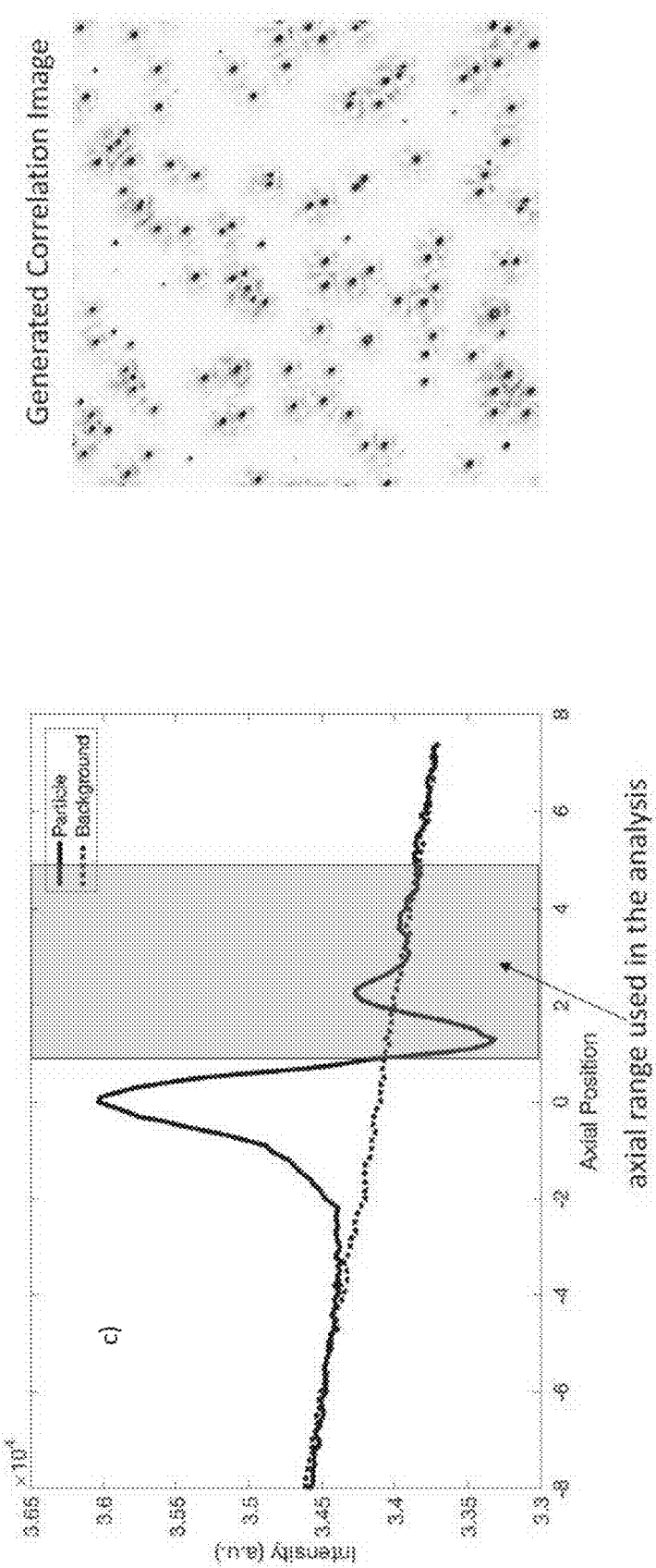
Figure 8H:
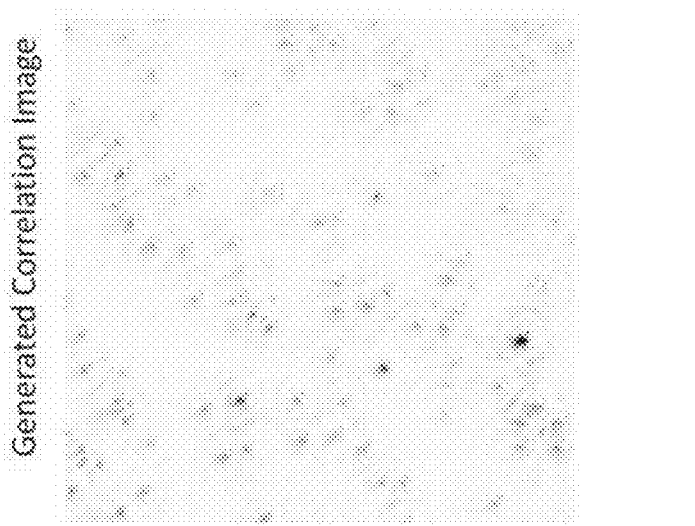
Figure 8G:
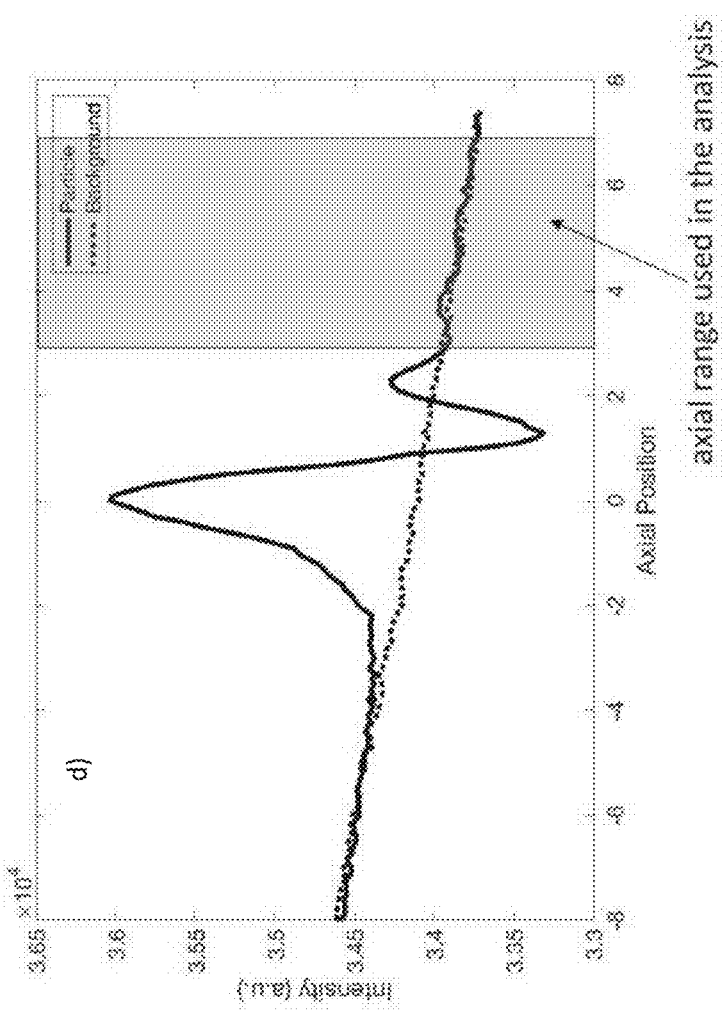

FIGS. 7A-7B show the sensitivity capability of the system for biological nanoparticles. Single unlabeled exosomes with a diameter of <50 nm to sample substrate (15) are coated. In FIG. 7A, conventional interferometric image of the sample is shown. Implementation of the depth scanning correlation technique significantly enhanced the visibility of the particles and improved the sensitivity limit as it can be seen in FIG. 7B.

FIGS. 8A-8H show the effect of analysis range on correlation image. During analysis, optimum analysis range is selected to have highest signal to noise ratio (SNR).

Figure 9:
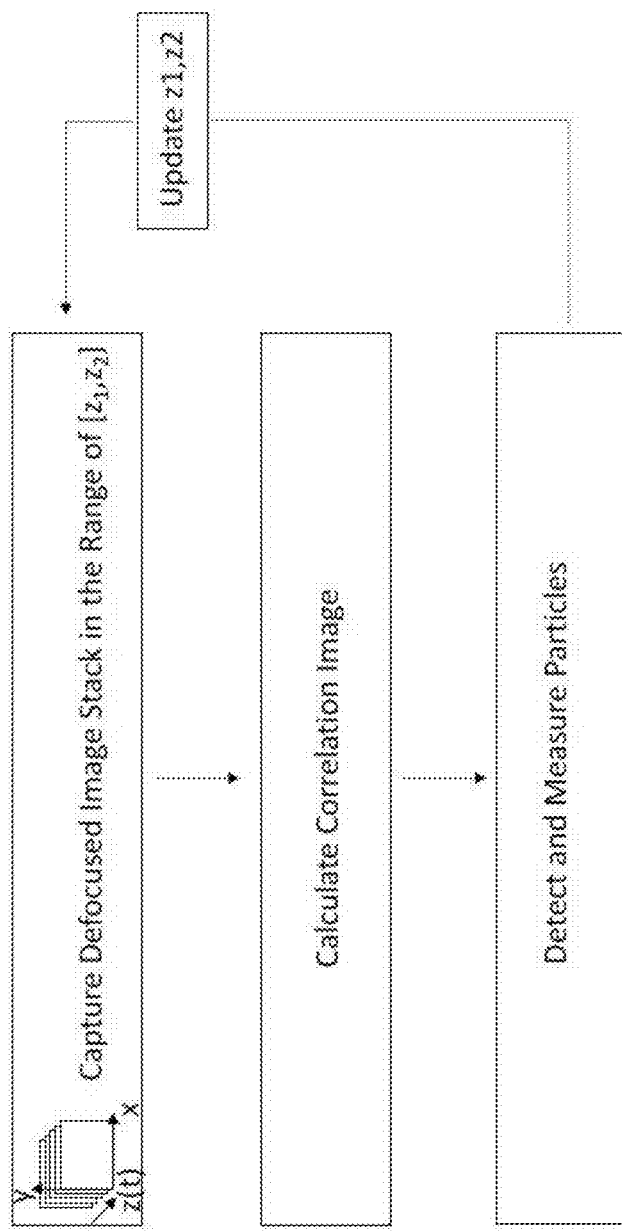
FIG. 9 shows the data acquisition and analysis flow chart in accordance with this invention.

FIG. 9 demonstrates data acquisition and analysis flow chart. First defocused image stack is captured, then correlation analysis is done to generate a correlation image. Once particles are detected and SNR for each particle is measured, defocusing range [z1, z2] is updated until the optimum SNR for the particle is calculated.

In a nutshell, the present invention proposes an imaging system (18) that works with much higher contrast and sensitivity compared to traditional microscopy instruments. With their unique defocusing response, a set of images are captured to gather more information about the requested pixels. Correlation image is provided through the correlation analysis. Correlation analysis involves actuation signal which moves the movable means (13), pixel intensity of nanoparticle and pixel intensity of background for all of the frames that are captured. It is experimented that the imaging system (18) can be used to direct detection of dielectric nanoparticles as small as 33 nm in diameter without using any optical or mechanical resonant behavior.

A particular feature, structure, or characteristic described herein in connection with one embodiment may be implemented within other embodiments without departing from the scope of the invention. In addition, it is to be noted that the location or arrangement of individual elements within each disclosed embodiment may be modified without departing from the scope of the invention. The detailed description is, therefore, not to be taken in a limiting sense, and the scope of the present invention is defined only by the appended claims to be interpreted along with the full range of equivalents to which the claims are entitled.

In one embodiment of the present invention, an imaging system (18) for detection of dielectric nanoparticles comprises at least one light source (11) for illumination, a camera (14) for image capture, an objective lens (16), a sample substrate (15) and a computing unit.

In a further embodiment of the present invention, said sample substrate (15) is capable of carrying sub-wavelength particles smaller than the diffraction resolution limit of the imaging system.

In a further embodiment of the present invention, said imaging system (18) comprises a movable means (13) which moves the sample substrate (15) in the axial direction such that depthwise different images are captured at different axial distances from the sample substrate (15) to said objective lens (16).

In a further embodiment of the present invention, said computing unit computes a correlation image using the depth images wherein the sub-wavelength particles become resolvable and appear with higher contrast in the correlation image.

In a further embodiment of the present invention, said light source (11) provides a nearly collimated illumination beam on the sample plate such that the background illumination on the images vary as the movable means (13) is moved.

In a further embodiment of the present invention, said light source (11) provides a collimated illumination beam on the sample substrate (15).

In a further embodiment of the present invention, said light source (11) provides an uncollimated illumination beam on the sample substrate (15).

In a further embodiment of the present invention, said light source (11) provides a converging beam on the sample substrate (15).

In a further embodiment of the present invention, said light source (11) provides a diverging beam on the sample substrate (15).

In a further embodiment of the present invention, said objective lens (16) provides magnification.

In a further embodiment of the present invention, said depthwise images are a collection of focused and defocused images.

In a further embodiment of the present invention, said sample substrate (15) reflects some of the scattered light creating reference light.

In a further embodiment of the present invention, said sample substrate (15) is inside a fluidic chamber.

In a further embodiment of the present invention, the particles are immobilized on top of said sample substrate (15).

In a further embodiment of the present invention, said sample substrate (15) is a flat surface.

In a further embodiment of the present invention, said sample substrate (15) is a non-flat surface.

In a further embodiment of the present invention, said the particles are immobilized on other larger particles which are resolvable in captured images.

In a further embodiment of the present invention, at least one light source (11) is an array of LEDs.

In a further embodiment of the present invention, LEDs are of the same or different wavelengths.

In a further embodiment of the present invention, the sample substrate (15) comprises a dielectric layer.

In a further embodiment of the present invention, dielectric layer thickness of the sample substrate (15) is adjusted according to the wavelength of illumination to provide maximum interference signal.

In a further embodiment of the present invention, sample comprising the immobilized nanoparticles on top of sample substrate (15) is illuminated by the light source (11) in wide field illumination configuration.

In a further embodiment of the present invention, correlation image is calculated using defocused images.

In a further embodiment of the present invention, correlation image is calculated using defocused and focused images.

In a further embodiment of the present invention, visibility of particles is improved by using difference of defocusing response of particles and background region.

In a further embodiment of the present invention, said imaging system (18) detects particles that are smaller than 100 nm.

In a further embodiment of the present invention, said imaging system (18) detects particles that are smaller than 50 nm.

In a further embodiment of the present invention, said imaging system (18) detects particles that are smaller than 100 nm and bigger than 10 nm.

In a further embodiment of the present invention, said imaging system (18) detects particles that are smaller than 100 nm and bigger than 10 nm.

In a further embodiment of the present invention, the particles are immersed in liquid.

In a further embodiment of the present invention, imaging system (18) detects particles that are extracellular vesicles such as exosomes In a further embodiment of the present invention, imaging system (18) detects particles that are cells, viruses, or bacteria.

What is claimed is:

1. An imaging system for a detection of nanoparticles, comprising at least one light source for illumination, a camera for image capture, an objective lens, a sample substrate and a computer; wherein
   the sample substrate comprises a structure carrying immobilized sub-wavelength particles smaller than a diffraction resolution limit of the imaging system,
   a reference light is provided by a first part of a light from the at least one light source reflected from the sample substrate, and a scattered light is provided by a second part of the light from the at least one light source scattered on the immobilized sub-wavelength particles,
   said objective lens is configured to collect said reference light and said scattered light such that the reference light and the scattered light interfere at the camera,
   the imaging system further comprises a movable platform actuatable by an actuation signal such that the movable platform moves the sample substrate in an axial direction to induce a change in an axial distance between the sample substrate and the objective lens such that depthwise different images are captured by the camera at different axial distances,
   said computer is configured to compute a correlation image including squares of correlation coefficients between the actuation signal of said movable platform and each pixel of the depthwise different images, and determine pixel intensity values of the correlation image using the depthwise different images, which are composed of focused and defocused images, based on the squares of the correlation coefficients, wherein the sub-wavelength particles are resolved and appear in the correlation image.

2. The imaging system according to claim 1, wherein the light source provides an illumination beam on the sample substrate such that a background illumination on the depthwise different images vary as the movable platform is moved.

3. The imaging system according to claim 2, wherein the light source provides a converging beam on the sample substrate.

4. The imaging system according to claim 2, wherein the light source provides a diverging beam on the sample substrate.

5. The imaging system according to claim 1, wherein the light source provides a collimated illumination beam on the sample substrate.

6. The imaging system according to claim 1, wherein the light source provides an uncollimated illumination beam on the sample substrate.

7. The imaging system according to claim 1, wherein the sample substrate is inside a fluidic chamber.

8. The imaging system according to claim 1, wherein the sample substrate is a flat surface.

9. The imaging system according to claim 1, wherein the sample substrate is a non-flat surface.

10. The imaging system according to claim 1, wherein the sub-wavelength particles are immobilized on top of other larger particles comprising biological molecules, and the reference light is created and interferes at the camera with the scattered light from the sub-wavelength particles.

11. The imaging system according to claim 1, wherein at least one light source is an array of LEDs comprising at least one LED.

12. The imaging system according to claim 11, wherein the LEDs are of the same or different wavelengths.

13. The imaging system according to claim 1, wherein the sample substrate comprises a dielectric layer.

14. The imaging system according to claim 1, wherein a dielectric layer thickness of the sample substrate is adjusted according to a wavelength of the illumination to provide a maximum interference signal.

15. The imaging system according to claim 1, wherein a sample comprising immobilized nanoparticles on a top of the sample substrate is illuminated by the light source in a wide field illumination configuration.

16. The imaging system according to claim 1, wherein a visibility of the nanoparticles is improved by using a difference of a defocusing response of the sub-wavelength particles and a background region.

17. The imaging system according to claim 1, wherein the sub-wavelength particles are smaller than 100 nm.

18. The imaging system according to claim 1, wherein the sub-wavelength particles are smaller than 50 nm.

19. The imaging system according to claim 1, wherein the sub-wavelength particles are smaller than 100 nm and bigger than 10 nm.

20. The imaging system according to claim 1, wherein the sub-wavelength particles are immersed in a liquid.

21. The imaging system according to claim 1, wherein the sub-wavelength particles are extracellular vesicles comprising exosomes or viruses.

22. The imaging system according to claim 1, wherein the sub-wavelength particles are cells, viruses, or bacteria.

23. The imaging system according to claim 1, wherein the camera forms an image using a scanning detector.

24. The imaging system according to claim 1, wherein a microscope objective compensates for aberrations when the sub-wavelength particles are immersed in a liquid.

* * * * *